(12) United States Patent
Chen et al.

(10) Patent No.: US 7,888,525 B2
(45) Date of Patent: Feb. 15, 2011

(54) METHOD FOR PREPARING ORGANIC CARBONATES

(75) Inventors: Min-Sheng Chen, Taipei (TW); Chia-Jung Tsai, Taipei (TW); Chih-Wei Chang, Taichung (TW)

(73) Assignee: China Petrochemical Development Corporation, Taipei (TW)

( * ) Notice: Subject to any disclaimer, the term of this patent is extended or adjusted under 35 U.S.C. 154(b) by 238 days.

(21) Appl. No.: 12/079,206

(22) Filed: Mar. 25, 2008

(65) Prior Publication Data

US 2008/0300419 A1  Dec. 4, 2008

(30) Foreign Application Priority Data

May 28, 2007  (TW) .............. 96118917 A

(51) Int. Cl.
*C07C 69/96* (2006.01)
(52) U.S. Cl. .................................... 558/260
(58) Field of Classification Search ............ 558/260
See application file for complete search history.

(56) References Cited

U.S. PATENT DOCUMENTS 4,218,391 A  8/1980  Romano et al.
4,318,862 A  3/1982  Romano et al.
4,370,275 A * 1/1983  Stammann et al. .......... 558/277
5,162,563 A  11/1992  Nishihira et al.

FOREIGN PATENT DOCUMENTS

| CN | 1197792 | 11/1998 |
| EP | 0460732 | 12/1991 |
| JP | 54-024827 | 2/1979 |

OTHER PUBLICATIONS

Jiang et al.,2003, CAS: 140:272673.*

* cited by examiner

*Primary Examiner*—Rei-tsang Shiao
(74) *Attorney, Agent, or Firm*—Peter F. Corless; Dwight D. Kim; Edwards Angell Palmer & Dodge LLP

(57) ABSTRACT

A method for preparing organic carbonates comprising subjecting an alcohol compound to oxidative carbonylation in the presence of carbon monoxide, oxygen and a liquid-phase catalytic system, to form a organic carbonates, wherein the liquid-phase catalytic system includes at least one catalyst, at least one additive and at least one ionic liquid composed of a cation, which has a nitrogen-containing heterocyclic structure, and an anion. Through using the additive and the ionic liquid, the activity and the performance of the catalyst are enhanced, and increased reaction rate and yield can be obtained.

12 Claims, No Drawings

METHOD FOR PREPARING ORGANIC CARBONATES

BACKGROUND OF THE INVENTION

1. Field of Invention

The present invention relates to a method for preparing organic carbonates, and more particularly, to a method of for preparing organic carbonates from an alcohol compound.

2. Description of Related Art

Organic carbonates find use as a solvent, a lubricant, a plasticizer and a monomer for organic glasses, and have been used in methylation and carbonylation process for preparing isocyanates, polyurethanes and polycarbonates. Furthermore, organic carbonates have been used as anti-explosive additive for gasoline or fuels heavier than gasoline.

Conventionally, organic carbonates are synthesized by phosgenation of methanol (phosgene route). However, phosgene is a toxic chemical and causes corrosion to the reactor, thus phosgene route has been gradually replaced by oxidative carbonylation of an alcohol in the presence of carbon monoxide and oxygen (oxidative carbonylation route) in recent years. Compared with phosgene route, oxidative carbonylation route has advantages such as easy acquirement of starting materials, simple synthetic procedures, less environmental pollution and lower production cost.

Oxidative carbonylation of an alcohol can be performed either in gas phase or in liquid phase. For gas-phase oxidative carbonylation of alcohols, one representative example is disclosed by U.S. Pat. No. 5,162,563, which comprises bringing carbon monoxide into contact with an ester of nitrous acid in a vapor phase in the presence of a solid catalyst, for example, $PdCl_2$ combined with copper.

For liquid-phase oxidative carbonylation of alcohols, various catalysts or catalyst systems have been proposed. For example, EP0460732 discloses using cuprous chloride (CuCl) as catalyst. U.S. Pat. No. 4,218,391 and U.S. Pat. No. 4,318,862 disclose a catalyst comprising a salt of a metal belonging to the Groups IB, IIB and VIIIB of the Periodic Table, preferably the salts of monovalent copper (for example CuCl and CuBr). In the process of these patents, in order to elevate reaction rate, it is necessary to use high concentration of cuprous chloride; however, such high concentration of cuprous chloride may cause corrosion to the reactor. To resolve this problem, the reactor is provided with glass liner on its inner wall. However, the presence of glass liner would enlarge the reactor, which was undesirable from the viewpoint of space utilization.

Chinese Patent CN1197792 discloses a two-component catalyst system for liquid-phase oxidative carbonylation of alcohols, comprising cuprous chloride as catalyst and one inorganic salt such as $MgCl_2$, $CaCl_2$, $ZnCl_2$, KCl etc. as additive. JP No. 54-24827 discloses a similar two-component catalyst system including cuprous oxide as catalyst and a halide of alkali metal or alkaline earth metal as additive. Although these two-component catalyst systems can increase the solubility of CuCl in the reaction medium, they still have the problem of corrosion to the reactor.

U.S. Pat. No. 4,370,275 discloses a catalyst comprising as the essential components, (a) copper and/or copper ions, (b) one or more anions selected from oxide anion, hydroxide anion and carbonate anion, (c) halide ions, and (d) one or more nitrogen bases. A representative catalyst system thereof comprises Cu(II)O, Cu(II)Cl$_2$ and pyridine.

The previous disclosed catalysts are still not satisfactory since the yield of organic carbonates is low and/or corrosion to the reactor may occur. Therefore, a method for preparing organic carbonates, which can increase the reaction rate and yield as well as reduce the problem of corrosion to the reactor, is desired.

SUMMARY OF THE INVENTION

It is an object of the present invention to provide a method for preparing organic carbonates wherein the activity of the catalyst is enhanced.

Another object of the present invention is to provide a method for preparing organic carbonates with high yield.

A further object of the present invention is to provide a method for preparing organic carbonates with reduced corrosion to the reactor.

To achieve the aforementioned and other objects, the present invention provides a method for preparing organic carbonates comprising subjecting an alcohol compound to oxidative carbonylation in the presence of carbon monoxide, oxygen and a liquid-phase catalytic system, to form a organic carbonates, wherein the liquid-phase catalytic system includes at least one catalyst, at least one additive and at least one ionic liquid composed of a cation, which has a nitrogen-containing heterocyclic structure, and an anion. Through using the additive and the ionic liquid, the activity and the performance of the catalyst can be enhanced, and higher reaction rate and yield can be obtained.

DETAILED DESCRIPTION OF THE PREFERRED EMBODIMENTS

The method of the present invention comprises subjecting an alcohol compound ROH (wherein R represents an optionally substituted alkyl, aryl, alkylaryl or aralkyl group) to oxidative carbonylation in the presence of carbon monoxide, oxygen and a liquid-phase catalytic system, to form a organic carbonates ($(RO)_2CO$). The reaction is shown as follows:

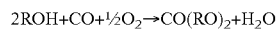

$$2ROH + CO + \tfrac{1}{2}O_2 \rightarrow CO(RO)_2 + H_2O$$

The alcohol compounds used in the method according to the present invention can be linear, branched or cyclic aliphatic alcohols having 1 to 30 carbon atoms, preferably 1 to 12 carbon atoms, more preferably 1 to 6 carbon atoms; an monohydroxy aromatic compound having 6 to 30 carbon atoms; or an multihydroxy aromatic compound having 6 to 30 carbon atoms. Examples of these alcohol compounds include, but are not limited to, methanol, ethanol, propanol, butanol and phenylmethanol. In one embodiment, methanol is subjected to oxidative carbonylation in the presence of carbon monoxide and oxygen, to form dimethyl carbonate.

The liquid-phase catalytic system used in this invention include at least one catalyst, at least one additive and at least one ionic liquid composed of a cation, which has a nitrogen-containing heterocyclic structure, and an anion.

The catalyst usually used in the liquid-phase catalytic system according to the present invention includes, for example, an organic or inorganic metal halide catalyst, such as organic or inorganic halides of palladium, platinum, copper, silver, gold, zinc, iron and nickel. Preferably, copper catalysts are used. The examples of the copper catalyst include, but are not limited to, cupric halides and/or cuprous halides, such as cupric chloride, cuprous chloride, cuprous bromide, cuprous iodide; and copper (II) dimethoxide.

In general, the amount of the catalyst is 0.1 to 30 wt %, preferably 0.1 to 10 wt %, based on the total weight of the reaction mixture comprising the alcohol compound, the catalyst, the additive and the ionic liquid. Furthermore, the copper catalyst is usually used at a concentration (calculated by copper) of 1 to 50000 ppm, preferably 2000 to 30000 ppm.

The liquid-phase catalytic system used in the method of this invention includes at least one additive, for example, monocyclic or dicyclic compounds containing one or two nitrogen atoms, for enhancing the conversion ratio of the alcohol compound and the selectivity of the reaction. The examples of the additive include, but are not limited to, imidazole compounds, benzimidazole compounds, pyridine compounds, bipyridyl compounds, pyridazine compounds, pyrimidine compounds or pyrazine compounds, which may be unsubstituted or substituted by halogen, nitro, cyano, amino, $C_{1-12}$ alkyl, $C_{1-12}$ alkylamino, $C_{1-12}$ alkoxy, $C_{1-12}$ alkanoyl, $C_{3-12}$ cycloalkyl, $C_{3-12}$ cycloalkyloxy, $C_{3-12}$ cycloalkylacyl, $C_{6-20}$ aryl, $C_{7-20}$ arylalkyl or $C_{7-20}$ alkylaryl, wherein $C_{1-12}$ alkyl, $C_{1-12}$ alkylamino, $C_{1-12}$ alkoxy, $C_{1-12}$ alkanoyl, $C_{3-20}$ cycloalkyl, $C_{3-20}$ cycloalkyloxy, $C_{3-20}$ cycloalkylacyl, $C_{6-20}$ aryl, $C_{7-20}$ arylalkyl and $C_{7-20}$ alkylaryl may be further substituted by halogen, nitro and/or cyano. The examples of the additive include 1-methylimidazole, 2-methylimidazole, 2-isopropylimidazole, 1,2-dimethylimidazole, 4,5-diphenylimidazole, pyridine, 2,2'-bipyridyl and 2-aminobenzimidazole.

In the method according to the present invention, the liquid-phase catalytic system may include one additive or the mixture of the plural additive. Usually, the additive are added in an amount of 0.1 to 10 times, preferably 0.2 to 5 times as many moles of the catalyst. Generally, the amount of the additive, is 0.1 to 30 wt %, preferably 0.1 to 10 wt %, based on the total weight of the reaction mixture comprising the alcohol compound, the catalyst, the additive and the ionic liquid.

The liquid-phase catalytic system according to the invention includes at least one ionic liquid composed of a cation and an anion, wherein the cation has a nitrogen-containing heterocyclic structure, for example, 5- or 6-membered heterocyclic structure containing one or two nitrogen atoms. In one preferred embodiment, the cation that forms the ionic liquid has a structure shown by the following formula (I);

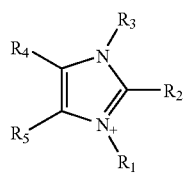

(I)

wherein, $R_1$ and $R_3$ are, independently, $C_{1-12}$ alkyl, $C_{1-12}$ alkylamino, $C_{1-12}$ alkoxy, $C_{1-12}$ alkanoyl, $C_{3-20}$ cycloalkyl, $C_{3-20}$ cycloalkyloxy, $C_{3-20}$ cycloalkylacyl, $C_{6-20}$ aryl, $C_{7-20}$ arylalkyl or $C_{7-20}$ alkylaryl, each of these groups may be further substituted by halogen, nitro and/or cyano; and $R_2$, $R_4$ and $R_5$ are, independently, hydrogen, halogen, nitro, cyano, amino, $C_{1-12}$ alkyl, $C_{1-12}$ alkylamino, $C_{1-12}$ alkoxy, $C_{1-12}$ alkanoyl, $C_{3-20}$ cycloalkyl, $C_{3-20}$ cycloalkyloxy, $C_{3-20}$ cycloalkylacyl, $C_{6-20}$ aryl, $C_{7-20}$ arylalkyl or $C_{7-20}$ alkylaryl, wherein $C_{1-12}$ alkyl, $C_{1-12}$ alkylamino, $C_{1-12}$ alkoxy, $C_{1-12}$ alkanoyl, $C_{3-20}$ cycloalkyl, $C_{3-20}$ cycloalkyloxy, $C_{3-20}$ cycloalkylacyl, $C_{6-20}$ aryl, $C_{7-20}$ arylalkyl or $C_{7-20}$ alkylaryl may be further substituted by halogen, nitro and/or cyano.

In another preferred embodiment, the cation that forms the ionic liquid has a structure shown by the following formula (II);

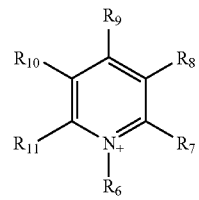

(II)

wherein, $R_6$ represents $C_{1-12}$ alkyl, $C_{1-12}$ alkylamino, $C_{1-12}$ alkoxy, $C_{1-12}$ alkanoyl, $C_{3-20}$ cycloalkyl, $C_{3-20}$ cycloalkyloxy, $C_{3-20}$ cycloalkylacyl, $C_{6-20}$ aryl, $C_{7-20}$ arylalkyl or $C_{7-20}$ alkylaryl, each of these groups may be optionally substituted by halogen, nitro and/or cyano; and $R_7$, $R_8$, $R_9$, $R_{10}$ and $R_{11}$, are, independently, hydrogen, halogen, nitro, cyano, amino, $C_{1-12}$ alkyl, $C_{1-2}$ alkylamino, $C_{1-12}$ alkoxy, $C_{1-12}$ alkylacyl, $C_{3-20}$ cycloalkyl, $C_{3-20}$ cycloalkyloxy, $C_{3-20}$ cycloalkylacyl, $C_{6-20}$ aryl, $C_{7-20}$ arylalkyl or $C_{7-20}$ alkylaryl, wherein $C_{1-12}$ alkyl, $C_{1-12}$ alkylamino, $C_{1-12}$ alkoxy, $C_{1-12}$ alkylacyl, $C_{3-20}$ cycloalkyl, $C_{3-20}$ cycloalkyloxy, $C_{3-20}$ cycloalkylacyl, $C_{6-20}$ aryl, $C_{7-20}$ arylalkyl and $C_{7-20}$ alkylaryl may be optionally substituted by halogen, nitro and/or cyano.

In the specification, the term "halogen" refers to fluorine, chlorine, bromine or iodine. The term "alkyl" refers to a linear, branched or cyclic alkyl group having 1 to 12, preferably 1 to 6 carbon atoms. The term "alkylamino" refers to a linear, branched or cyclic alkylamino group having 1 to 12, preferably 1 to 6 carbon atoms. The term "alkoxy" refers to a linear, branched or cyclic alkoxy group having 1 to 12, preferably 1 to 6 carbon atoms. The term "alkanoyl" refers to a linear, branched or cyclic alkanoyl group having 1 to 12, preferably 1 to 6 carbon atoms. The term "$C_{3-20}$ cycloalkyl" refers to a cyclic alkyl group having 3 to 20, preferably 3 to 12 carbon atoms. The term "cycloalkyloxy" refers to a cycloalkyloxy having 3 to 20, preferably 3 to 12 carbon atoms. The term "$C_{3-20}$ cycloalkylacyl" refers to a cycloalkylacyl having 3 to 20, preferably 3 to 12 carbon atoms. The term "aryl" refers to an aryl group having 6 to 20, preferably 6 to 12 carbon atoms. The term "arylalkyl" refers to an arylalkyl group having 7 to 20, preferably 7 to 12 carbon atoms. The term "$C_{7-20}$ alkylaryl" refers to an alkylaryl group having 7 to 20, preferably 7 to 12 carbon atoms.

Examples of the anion that forms the ionic liquid include, but are not limited to, $F^-$, $Cl^-$, $Br^-$, $I^-$, $PF_6^-$, $SCN^-$, $HSO_4^-$, $CH_3SO_3^-$, $CH_3SO_4^-$, $AlCl_4^-$, $Al_2Cl_7^-$, $Al_3Cl_{10}^-$, $CH_3CH_2SO_4^-$, $CuCl_2^-$, $Cu_2Cl_3^-$ or $BF_4^-$, preferably $Cl^-$, $Br^-$, $PF_6^-$ or $BF_4^-$.

The liquid-phase catalytic system according to the present invention may include one ionic liquid or a mixture of plural ionic liquids. The amount of the ionic liquid is usually 0.1 to 80 wt %, preferably 1 to 40 wt %, based on the total weight of the reaction mixture comprising the alcohol compound, the catalyst, the additive and the ionic liquid.

Through using the ionic liquid, the undesired effects of volatile solvents can be avoided; in addition, the activity of the catalyst, the selectivity of the reaction and the yield of organic carbonates can be further increased.

The oxidative carbonylation of alcohol is usually conducted at a temperature of 60° C. to 200° C., preferably 100° C. to 140° C., and at a pressure of 10 to 80 kg/cm², preferably of 20 to 30 kg/cm².

The following embodiments further illustrate the features and the effects of the invention, but the invention is not limited thereto.

EXAMPLE

The conversion ratio, selectivity and yield in the Examples are calculated as follows:

Conversion ratio (%)=consumed alcohol (mol)/alcohol feed (mol)×100%

Selectivity (%)=2×produced organic carbonates (mol)/consumed alcohol (mol)×100%

Yield (%)=conversion ratio (%)×selectivity (%)×100%

Comparative Example 1

Methanol and cuprous chloride in an amount as listed in Table 1 were fed into a 1 L stainless steel-made, Teflon-lined, high pressure reactor provided with a stirrer. The nitrogen gas was introduced to the reactor to replace the air therein. After the reaction system was pressed with nitrogen to 25 kg/cm² and heated to 120° C., a mixture of carbon monoxide and oxygen gas was introduced to the reactor with stirring. The concentration of cuprous chloride catalyst was 16492 ppm (calculated by Cu). After the reaction was conducted for 1 hour, the product was analyzed by gas chromatography. The conversion ratio of methanol, the selectivity of the reaction and the yield of dimethyl carbonate were calculated and reported in Table 1.

Comparative Example 2

Methanol, cuprous chloride (as catalyst) and 2-methylimidazole (as additive) in an amount as listed in Table 1 were fed into a 1 L stainless steel-made, Teflon-lined, high pressure reactor provided with a stirrer. The nitrogen gas was introduced to the reactor to replace the air therein. After the reaction system was pressed with nitrogen to 25 kg/cm² and heated to 120° C., a mixture of carbon monoxide and oxygen gas was introduced to the reactor with stirring. The concentration of cuprous chloride catalyst was 16492 ppm (calculated by Cu). After the reaction was conducted for 1 hour, the product was analyzed by gas chromatography. The conversion ratio of methanol, the selectivity and the reaction and the yield of dimethyl carbonate were calculated and reported in Table 1.

Example 1

Methanol, cuprous chloride, 2-methylimidazole (as additive) and 1-butyl-3-methylimidazolium chloride ([Bmim][Cl])(as ionic liquid) in an amount as listed in Table 1 were fed into a 1 L stainless steel-made, Teflon-lined, high pressure reactor provided with a stirrer. The nitrogen gas was introduced to the reactor to replace the air therein. After the reaction system was pressed with nitrogen to 25 kg/cm² and heated to 120° C., a mixture of carbon monoxide and oxygen gas was introduced to the reactor. The concentration of cuprous chloride catalyst was 16492 ppm (calculated by Cu). After reacting for 1 hour, the product was analyzed by gas chromatography. The conversion ratio of methanol, the selectivity of the reaction and the yield of dimethyl carbonate were calculated and reported in Table 1.

Examples 2 to 9

The procedures of Example 1 were repeated except the kind and the amount of the additive and/or the ionic liquid were varied as listed in Table 1. After the reaction was conducted for 1 hour, the product was analyzed by gas chromatography. The conversion ratio of methanol, the selectivity of the reaction and the yield of dimethyl carbonate were calculated and reported in Table 1.

TABLE 1

| | Comparative Example 1 | Comparative Example 2 | Example 1 | Example 2 | Example 3 | Example 4 | Example 5 | Example 6 | Example 7 | Example 8 | Example 9 |
|---|---|---|---|---|---|---|---|---|---|---|---|
| Methanol (wt %) | 97.3 | 91.2 | 80.4 | 79.4 | 78.5 | 75 | 80.8 | 79.1 | 77.2 | 77.7 | 72.3 |
| Cuprous chloride (wt %) | 2.7 | 2.7 | 2.7 | 2.7 | 2.7 | 2.7 | 2.7 | 2.7 | 2.7 | 2.7 | 2.7 |
| 2-methylimidazole (wt %) | | 6.1 | 6.1 | | | | | 6.1 | 6.1 | 6.1 | |
| 1,2-dimethylimidazolium chloride (wt %) | | | | 7.1 | | | | | | | |
| 2-isopropylimidazole (wt %) | | | | | 8.0 | | | | | | |
| 2,2'-bipyridyl (wt %) | | | | | | 11.5 | | | | | 11.5 |
| Pyridine (wt %) | | | | | | | 5.7 | | | | |
| [Bmin][Cl]*¹ (wt %) | | | 10.8 | 10.8 | 10.8 | 10.8 | 10.8 | | | | |
| [BMmim][Cl]*² (wt %) | | | | | | | | 12.1 | | | |
| [Bmin][BF₄]*³ (wt %) | | | | | | | | | 14.0 | | |
| [Py][Br]*⁴ (wt %) | | | | | | | | | | 13.5 | 13.5 |
| Total weight of reaction mixture | 100 | 100 | 100 | 100 | 100 | 100 | 100 | 100 | 100 | 100 | 100 |
| CO (%) | 87 | 87 | 87 | 87 | 87 | 87 | 87 | 87 | 87 | 87 | 87 |
| O₂ (%) | 13 | 13 | 13 | 13 | 13 | 13 | 13 | 13 | 13 | 13 | 13 |
| Conversion ratio (%) | 14.8 | 24.14 | 32.4 | 31.2 | 26.9 | 31.1 | 31.9 | 27.3 | 29.9 | 31.7 | 28.7 |

TABLE 1-continued

|  | Comparative Example 1 | Comparative Example 2 | Example 1 | Example 2 | Example 3 | Example 4 | Example 5 | Example 6 | Example 7 | Example 8 | Example 9 |
|---|---|---|---|---|---|---|---|---|---|---|---|
| Selectivity (%) | 79.4 | 79.25 | 96.0 | 92.7 | 78.1 | 88.6 | 99.0 | 78.6 | 89.8 | 96.5 | 87.9 |
| Yield (%) | 11.8 | 19.13 | 31.1 | 28.9 | 21.0 | 27.6 | 31.6 | 21.5 | 26.9 | 30.6 | 25.2 |

*[1][Bmim][Cl] represents 1-butyl-3-methyl imidazolium chloride
*[2][BMmim][Cl] represents 1-butyl-2,3-dimehtyl imidazolium chloride
*[3][Bmim][BF_4] represents 1-butyl-3-methyl imidazolium tetrafluoroborate
*[4][Py][Br] represents 1-butylpyridinium bromide As shown in Table 1, compared with Comparative Examples wherein no ionic liquid was added, the method according to the present invention has increased conversion ratio and higher selectivity of the reaction and hence higher yield of dimethyl carbonate can be obtained.

Example 10

Methanol, cuprous chloride, 2-methylimidazole (as additive) and 1-butyl-3-methylimidazolium chloride ([Bmim][Cl])(as ionic liquid) in an amount as listed in Table 2 were fed into a 1 L stainless steel-made, Teflon-lined, high pressure reactor provided with a stirrer. The nitrogen gas was introduced to the reactor to replace the air therein. After the reaction system was pressed with nitrogen to 25 kg/cm$^2$ and heated to 120° C., a mixture of carbon monoxide and oxygen gas was introduced to the reactor. The concentration of cuprous chloride catalyst was 16492 ppm (calculated by Cu). After the reaction was conducted for 1 hour, the product was analyzed by gas chromatography. The conversion ratio of methanol, the selectivity of the reaction and the yield of dimethyl carbonate were calculated and reported in Table 2.

Example 11

Methanol, cuprous iodide, 2-methylimidazole (as additive) and 1-butyl-3-methylimidazolium chloride ([Bmim][Cl])(as ionic liquid) in an amount as listed in Table 2 were fed into a 1 L stainless steel-made, Teflon-lined, high pressure reactor provided with a stirrer. The nitrogen gas was introduced to the reactor to replace the air therein. After the reaction system was pressed with nitrogen to 25 kg/cm$^2$ and heated to 120° C., a mixture of carbon monoxide and oxygen gas was introduced to the reactor. The concentration of cuprous iodide catalyst was 16492 ppm (calculated by Cu). After the reaction was conducted for 1 hour, the product was analyzed by gas chromatography. The conversion ratio of methanol, the selectivity of the reaction and the yield of dimethyl carbonate were calculated and reported in Table 2.

Example 12

Methanol, cuprous chloride, 2-methylimidazole (as additive) and 1-butyl-3-methylimidazolium chloride ([Bmim][Cl]) (as ionic liquid) in an amount as listed in Table 2 were fed into a 1 L stainless steel-made, Teflon-lined, high pressure reactor provided with a stirrer. The nitrogen gas was introduced to the reactor to replace the air therein. After the reaction system was pressed with nitrogen to 25 kg/cm$^2$ and heated to 120° C., a mixture of carbon monoxide and oxygen gas was introduced to the reactor. The concentration of cuprous chloride catalyst was 33163 ppm (calculated by Cu). After the reaction was conducted for 1 hour, the product was analyzed by gas chromatography. The conversion ratio of methanol, the selectivity of the reaction and the yield of dimethyl carbonate were calculated and reported in Table 2.

TABLE 2

|  | Comparative Example 1 | Comparative Example 2 | Example 1 | Example 10 | Example 11 | Example 12 | Example 13 | Example 14 | Example 15 | Example 16 | Example 17 |
|---|---|---|---|---|---|---|---|---|---|---|---|
| Methanol (wt %) | 97.3 | 91.2 | 80.4 | 84.4 | 78.1 | 77.7 | 81.2 | 59.5 | 80.4 | 80.4 | 80.4 |
| Cuprous chloride (wt %) | 2.7 | 2.7 | 2.7 | 2.7 |  | 5.4 | 1.9 | 1.9 | 2.7 | 2.7 | 2.7 |
| Cuprous iodide (wt %) |  |  |  |  | 5.0 |  |  |  |  |  |  |
| 2-methylimidazole (wt %) |  | 6.1 | 6.1 | 2.1 | 6.1 | 6.1 | 6.1 | 6.1 | 6.1 | 6.1 | 6.1 |
| [Bmim][Cl]*[1] (wt %) |  |  | 10.8 | 10.8 | 10.8 | 10.8 | 10.8 | 32.5 | 10.8 | 10.8 | 10.8 |
| Total weight of reaction mixture | 100 | 100 | 100 | 100 | 100 | 100 | 100 | 100 | 100 | 100 | 100 |
| CO (%) | 87 | 87 | 87 | 87 | 87 | 79 | 90 | 90 | 87 | 87 | 87 |
| O$_2$ (%) | 13 | 13 | 13 | 13 | 13 | 21 | 10 | 10 | 13 | 13 | 13 |
| Conversion ratio (%) | 14.8 | 24.14 | 32.4 | 31.1 | 27.5 | 25.6 | 22.9 | 23.6 | 30.3 | 22.0 | 30.6 |
| Selectivity (%) | 79.4 | 79.25 | 96.0 | 93.4 | 81.7 | 66.8 | 87.7 | 90.0 | 90.9 | 84.5 | 91.8 |
| Yield (%) | 11.8 | 19.13 | 31.1 | 29.0 | 22.5 | 17.1 | 20.1 | 21.2 | 27.5 | 18.6 | 28.1 |

Examples 13, 14

Methanol, cuprous chloride, 2-methylimidazole (as additive) and 1-butyl-3-methylimidazolium chloride ([Bmim]

[Cl])(as ionic liquid) in an amount as listed in Table 2 were fed into a 1 L stainless steel-made, Teflon-lined, high pressure reactor provided with a stirrer. The nitrogen gas was introduced to the reactor to replace the air therein. After the reaction system was pressed with nitrogen to 25 kg/cm$^2$ and heated to 120° C., a mixture of carbon monoxide and oxygen gas was introduced to the reactor. The concentration of the catalyst, cuprous chloride, was 11676 ppm. After the reaction was conducted for 1 hour, the product was analyzed by gas chromatography. The conversion ratio of methanol, the selectivity of the reaction and the yield of dimethyl carbonate were calculated and reported in Table 2.

Example 15

The procedures of Example 1 were repeated except the temperature of the reaction system was elevated to 140° C. After the reaction was conducted for 1 hour, the product was analyzed by gas chromatography. The conversion ratio of methanol, the selectivity of the reaction and the yield of dimethyl carbonate were calculated and reported in Table 2.

Example 16

The procedures of Example 1 were repeated except the pressure of the reaction system was reduced to 20 kg/cm$^2$. After the reaction was conducted for 1 hour, the product was analyzed by gas chromatography. The conversion ratio of methanol, the selectivity of the reaction and the yield of dimethyl carbonate were calculated and reported in Table 2.

Example 17

The procedures of Example 1 were repeated except the pressure of the reaction system was elevated to 30 kg/cm$^2$. After the reaction was conducted for 1 hour, the product was analyzed by gas chromatography. The conversion ratio of methanol, the selectivity of the reaction and the yield of dimethyl carbonate were calculated and reported in Table 2.

As shown in Table 2, using cuprous iodide as catalyst (Example 11) also elevates the conversion ratio of methanol and the selectivity of the reaction. Furthermore, increasing the amount of ionic liquid in the reaction system as in Examples 13 and 14, also elevates the conversion ratio of methanol, the selectivity of the reaction and the yield of dimethyl carbonate.

What is claimed is:

1. A method for preparing organic carbonates comprising subjecting an alcohol compound to oxidative carbonylation in the presence of carbon monoxide, oxygen and a liquid-phase catalytic system, to form a organic carbonates of the formula CO(RO)$_2$, wherein R representing an alkyl having 1 to 6 carbon atoms, and wherein the liquid-phase catalytic system includes at least one catalyst, at least one additive, and at least one ionic liquid composed of a cation and an anion, and wherein the catalyst is a copper catalyst, the additive is selected from the group consisting of an imidazole compound, a benzimidazole compound, a pyridine compound, a bipyridyl compound, a pyridazine compound, a pyrimidine compound, a pyrazine compound and a mixture thereof, and the cation of the ionic liquid has a structure of formula (I) or (II):

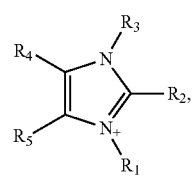

wherein R$_1$ and R$_3$ are, independently, C$_{1-12}$ alkyl, C$_{1-12}$ alkylamino, C$_{1-12}$ alkoxy, C$_{1-12}$ alkanoyl, C$_{3-20}$ cycloalkyl, C$_{3-20}$ cycloalkyloxy, C$_{3-20}$ cycloalkylacyl, C$_{6-20}$ aryl, C$_{7-20}$ arylalkyl or C$_{7-20}$ alkylaryl, each of these groups may be further substituted by halogen, nitro and/or cyano, and R$_2$, R$_4$ and R$_5$ are, independently, hydrogen, halogen, nitro, cyano, amino, C$_{1-12}$ alkyl, C$_{1-12}$ alkylamino, C$_{1-12}$ alkoxy, C$_{1-12}$ alkanoyl, C$_{3-20}$ cycloalkyl, C$_{3-20}$ cycloalkyloxy, C$_{3-20}$ cycloalkylacyl, C$_{6-20}$ aryl, C$_{7-20}$ arylalkyl or C$_{7-20}$ alkylaryl, wherein C$_{1-12}$ alkyl, C$_{1-12}$ alkylamino, C$_{1-12}$ alkoxy, C$_{1-12}$ alkanoyl, C$_{3-20}$ cycloalkyl, C$_{3-20}$ cycloalkyloxy, C$_{3-20}$ cycloalkylacyl, C$_{6-20}$ aryl, C$_{7-20}$ arylalkyl or C$_{7-20}$ alkylaryl may be further substituted by halogen, nitro and/or cyano; and

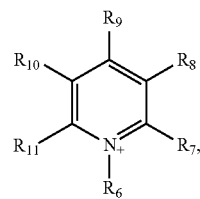

wherein R$_6$ represents C$_{1-12}$ alkyl, C$_{1-12}$ alkylamino, C$_{1-12}$ alkoxy, C$_{1-12}$ alkanoyl, C$_{3-20}$ cycloalkyl, C$_{3-20}$ cycloalkyloxy, C$_{3-20}$ cycloalkylacyl, C$_{6-20}$ aryl, C$_{7-20}$ arylalkyl or C$_{7-20}$ alkylaryl, each of these groups may be further substituted by halogen, nitro and/or cyano, and R$_7$, R$_8$, R$_9$, R$_{10}$ and R$_{11}$ are, independently, hydrogen, halogen, nitro, cyano, amino, C$_{1-12}$ alkyl, C$_{1-12}$ alkylamino, C$_{1-12}$ alkoxy, C$_{1-12}$ alkylacyl, C$_{3-20}$ cycloalkyl, C$_{3-20}$ cycloalkyloxy, C$_{3-20}$ cycloalkylacyl, C$_{6-20}$ aryl, C$_{7-20}$ arylalkyl or C$_{7-20}$ alkylaryl, wherein C$_{1-12}$ alkyl, C$_{1-12}$ alkylamino, C$_{1-12}$ alkoxy, C$_{1-12}$ alkylacyl, C$_{3-20}$ cycloalkyl, C$_{3-20}$ cycloalkyloxy, C$_{3-20}$ cycloalkylacyl, C$_{6-20}$ aryl, C$_{7-20}$ arylalkyl and C$_{7-20}$ alkylaryl may be further substituted by halogen, nitro and/or cyano.

2. The method according to claim 1, wherein the alcohol compound is selected from the group consisting of methanol, ethanol, propanol and butanol.

3. The method according to claim 1, wherein the catalyst is cupric halide and/or cuprous halide.

4. The method according to claim 1, wherein the catalyst is selected from the group consisting of cupric chloride, cuprous chloride, cuprous bromide, cuprous iodide, copper (II) dimethoxide and a mixture thereof.

5. The method according to claim 1, wherein the catalyst is used in an amount of 0.1 to 30% by weight based on the total weight of the reaction mixture.

6. The method according to claim 1, wherein the additive is used in an amount of 0.1 to 30% by weight based on the total weight of the reaction mixture.

7. The method according to claim 1, wherein the cation of the ionic liquid is selected from the group consisting of alkyl-substituted pyridinium cation and alkyl-substituted imidazolium cation.

8. The method according to claim 1, wherein the anion of the ionic liquid is selected from the group consisting of $F^-$, $Cl^-$, $Br^-$, $I^-$, $PF_6^-$, $SCN^-$, $HSO_4^-$, $CH_3SO_3^-$, $CH_3SO_4^-$, $AlCl_4^-$, $Al_2Cl_7^-$, $Al_3Cl_{10}^-$, $CH_3CH_2SO_4^-$, $CuCl_2^-$, $Cu_2Cl_3^-$ and $BF_4^-$.

9. The method according to claim 1, wherein the ionic liquid is used in an amount of 0.1 to 80% by weight based on the total weight of the reaction mixture.

10. The method according to claim 1, wherein the ionic liquid is used in an amount of 1 to 40% by weight based on the total weight of the reaction mixture.

11. The method according to claim 1, wherein oxidative carbonylation of the alcohol compound is conducted at a temperature of 60° C. to 200° C.

12. The method according to claim 1, wherein oxidative carbonylation of the alcohol compound is conducted at a pressure of 10 kg/cm² to 80 kg/cm².

* * * * *